United States Patent [19]

LeVeen et al.

[11] 4,312,343

[45] Jan. 26, 1982

[54] SYRINGE

[76] Inventors: Harry H. LeVeen, 800 Poly Pl., Brooklyn, N.Y. 11209; Robert F. LeVeen, 122 S. 51st St., Omaha, Nebr. 68132

[21] Appl. No.: 61,642

[22] Filed: Jul. 30, 1979

[51] Int. Cl.$^3$ ............................................. A61M 5/00
[52] U.S. Cl. ................................. 128/218 C; 128/234
[58] Field of Search ........... 128/218 C, 218 R, 218 P, 128/218 PA, 234, 236; 222/386, 390

[56] References Cited

U.S. PATENT DOCUMENTS

| | | | |
|---|---|---|---|
| 858,669 | 7/1907 | Radtke | 222/390 |
| 949,163 | 2/1910 | Stapley | 222/390 |
| 1,390,078 | 9/1921 | Blain | 222/390 |
| 4,153,056 | 5/1979 | Silver et al. | 128/218 C |
| 4,189,065 | 2/1980 | Herold | 128/236 X |

*Primary Examiner*—John D. Yasko
*Attorney, Agent, or Firm*—Brooks, Haidt, Haffner & Delahunty

[57] ABSTRACT

A syringe comprising a cylindrical barrel with a wall at one end with a nozzle and with a threaded actuating rod extending from its other end. The rod has a piston at the end thereof within the barrel, the piston being in fluid tight engagement with the inner wall of the barrel, and has a knob at its opposite end for rotating the rod. The rod also carries a collar with threads which mate with the rod threads, and the collar has slots which engage projections on the barrel and prevent movement of the collar relative to the barrel but which permit the collar to be disengaged readily from the barrel. Rotation of the rod causes movement of the piston axially of the barrel when the collar is engaged, but the rod can be moved axially without rotation when the collar is disengaged.

2 Claims, 4 Drawing Figures

SYRINGE

This invention relates to a syringe for precisely dispensing or withdrawing fluids against relatively high fluid resistance and particularly, to a syringe which can dispense a fluid in precisely metered amounts and under relatively high pressure with only small manual forces.

Syringes are well known in the medical art and are commonly used to supply a liquid to a vein or body cavity or to a device such as a catheter. Syringes are also used to suck up measured amounts of liquid.

Such syringes include a hollow cylinder or barrel with an opening or nozzle at one end and a piston or plunger therein which is slidable within the cylinder by means of a manually engageable rod or shaft extending from the opposite end of the cylinder. The piston has fluid tight engagement with the inner wall of the cylinder so that as the piston is moved toward the nozzle, liquid may be ejected from the nozzle and as the piston is moved away from the nozzle, liquid may be sucked into the cylinder through the nozzle. The nozzle may be connected to a needle, a catheter or other device.

In some cases, the liquid encounters relatively high opposing resistance when it is being dispensed from the cylinder, and the manual pressure required to move the piston is relatively high. If the piston and its actuator are moved with respect to the cylinder, by manually pushing the actuator it is difficult to dispense the liquid manually and to dispense it in precise amounts. Also, during the movement of the piston, the back pressure may vary which can make the movement of the piston erratic even though the manual pressure applied thereto is relatively constant.

It has been proposed to attach such a syringe to an actuator which has a ratchet and a forward movement limiting device so as to precisely control the amounts of liquid dispensed with movement of the plunger. See, for example, U.S. Pat. No. 4,022,207. Such an actuator not only is relatively expensive and cannot, therefore, be disposed of after use, but also is relatively awkward to use. Furthermore, the manually applied forces must be greater than the back pressure on the liquid, and with variations in the back pressure the liquid flow varies.

One object of the invention is to provide a self-contained syringe which permits the transport of fluid through the syringe opening, i.e., fluid flow out of or into the syringe, in precise quantities and with steady flow even though the fluid flow resistance externally of the syringe is high. Such fluid flow is obtained with relatively low manual forces.

Another object of the invention is to provide such a syringe which may be quickly and easily filled with the fluid to be transported through the syringe opening.

It is also an object of the invention to provide such a syringe which is of such simple construction and economical manufacture that it can be dispensed in a sterile package and be disposed of after use.

In accordance with the preferred embodiment of the invention, the syringe comprises a hollow cylinder with a wall at one end having an opening through which the fluid is transported. The opposite end of the hollow cylinder is open and receives a piston rotatably mounted on one end of a threaded rod having a knurled knob at its opposite end. The rod carries a collar having a threaded portion which mates with the thread on the rod. The opposite end of the cylinder has a pair of projections which interfits with a portion of the collar so that after the cylinder is partially filled with the fluid to be transported and the piston is in the cylinder, the collar can be rotated on the rod until it engages the projections which prevents further movement of the collar axially of the cylinder. When the rod is thereafter rotated by means of the knob, the piston moves axially of the cylinder to dispense the fluid through the opening in the end wall thereof. If the syringe is to be used to suck up fluid, the piston is inserted into the empty cylinder below the opposite end thereof, the collar is engaged with the projections and the threaded rod is rotated in the opposite direction to move the piston away from the end wall.

Other objects and advantages of the present invention will be apparent from the following detailed description of the presently preferred embodiments thereof, which description should be considered in conjunction with the accompanying drawing in which.

Figure 1:
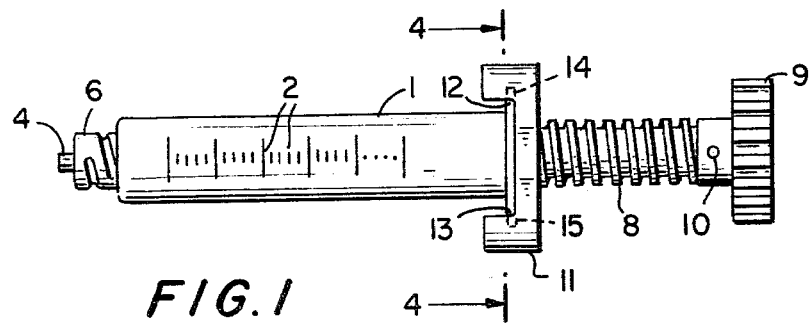
FIG. 1 is a side view of the preferred embodiment of the invention.
Figure 2:
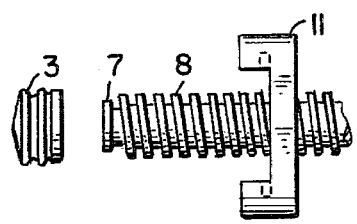
FIG. 2 is a fragmentary side view of the threaded rod, the collar and the piston forming part of the preferred embodiment, the piston being removed from the rod.
Figure 3:
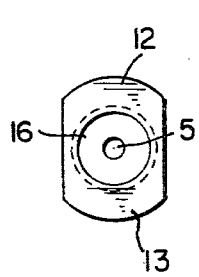
FIG. 3 is an end view of the cylinder of the preferred embodiment.
Figure 4:
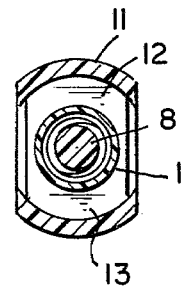
FIG. 4 is a cross-sectional view of the preferred embodiment and is taken along the line 4—4 indicated in FIG. 1.

The syringe illustrated in the figures of the drawing comprises a cylinder 1 made of a transparent or semi-transparent plastic material permitting visual observation of the contents therein. Graduations 2 are provided on the outer surface of the cylinder 1 to permit measurement of the movement of the piston 3 and hence, of the volume of fluid transported through the nozzle 4 having an opening 5 and surrounded by a sleeve 6 having threads for attaching other devices, such as a catheter, to the syringe. The piston 3 fits snugly within the bore of the cylinder 1 to provide a fluid tight engagement with the interior wall thereof and is made of a resilient material, such as neoprene rubber. The piston 3 is formed internally so that it snaps over a ridge 7 at the end of the threaded rod 8 and so that it does not rotate when the rod 8 is rotated.

The rod 8 extends from the end of the cylinder 1 opposite from the end thereof having the nozzle 4 and the opening 5 and has a knurled knob 9 at the end thereof opposite from the end of the rod 8 which carries the piston 3. The knob 9 may be integral with the rod 8 or may be secured thereto, such as by means of a pin 10. Preferably, the rod 8 and the knob 9 are molded from a plastic material, such as polypropylene.

The rod 8 carries a collar 11, which may be made of the same material as the rod 8, and which has a threaded bore, the threads of which mate with the threads on the rod 8. Preferably, the fit of the threads is such that when the collar 11 is disengaged from projections 12 and 13 on the cylinder 1, the collar 11 can be spun to permit rapid adjustment of the collar 11 in the axial direction of the rod 8.

The projections 12 and 13 on the cylinder 1 and slots 14 and 15 in the collar 11 form co-operating and interengaging means for releasably securing the collar 11 to the cylinder 1. The diameter of the projections 12 and 13 preferably is slightly larger than the internal diameter of the slots 14 and 15 or the axial dimensions of the slots 14 and 15 preferably is slightly less than the axial dimensions of the projections 12 and 13, or both, so that when the projections 12 and 13 are in the slots 14 and 15 the friction therebetween will prevent rotation of the collar 11 with rotation of the rod 8. However, the collar 11 and the projections 12 and 13 are shaped as indicated in the drawing and the dimensions of the slots 14 and 15 and the projections 12 and 13 are such that the collar 11 can be disengaged from the cylinder 1 by manually rotating the collar 11 by one-quarter of a turn with respect to the cylinder 1. When so released, the rod 8 and the piston 3 can be inserted in, or removed from the cylinder 1 by movement of the rod 8 axially of the cylinder 1 and without rotation of the rod 8.

When the projections 12 and 13 are in the slots 14 and 15 and the rod 8 is rotated by means of the knob 9, the piston 3 moves axially of the cylinder 1 without rotation of the piston 3.

In the use of the syringe of the invention for dispensing fluids, the collar 11 is disengaged from the cylinder 1 by turning the collar 11 with respect to the cylinder 1 until the projections 12 and 13 are out of the slots 14 and 15. The rod 8 is then moved axially of the cylinder 1 without rotation of the rod 8 until the collar 11 clears the projections 12 and 13, and then, the collar 11 is rotated on the rod 8 until the distance between the collar 11 and the piston 3 is sufficient to permit the piston 3 to engage, or almost engage, the wall of the cylinder 1 having the opening 5. The piston 3 is then moved axially of the interior of the cylinder 1 until it is at or near said wall and the nozzle 4, or any attachment thereto, having a fluid channel with a fluid receiving opening is immersed in the desired fluid. With the collar 11 still released from the projections 12 and 13, the rod 8 is moved to the right, as viewed in FIG. 1, without rotation of the rod 8 until the desired quantity of the fluid is sucked into the cylinder 1. The collar 11 is then rotated on the rod 8 until the projections 12 and 13 are received in the slots 14 and 15. Thereafter, when it is desired to dispense the fluid through the nozzle 4, the rod 8 is rotated (clockwise as viewed from the knob 9 end of the threads when the threads on the rod 8 are right hand threads) causing the rod 8 and the piston 3 to move to the left as viewed in FIG. 1 and thereby causing the fluid to flow out of the nozzle 4. The mechanical advantage obtained and the degree of movement of the piston 3 with rotation of the rod 8 depends, of course, on the pitch of the threads on the rod 8. Preferably the pitch of the threads is shallow, e.g. of the order of eight threads per inch, and acme threads are used.

With the syringe of the invention, the position of the piston 3 can be controlled precisely and hence, the amount of fluid dispensed can be controlled precisely. In addition, because of the mechanical advantage provided by the threads, the fluid can be dispensed under relatively high pressure without the use of large manual forces on the knob 9. Also, if the fluid flow resistance suddenly decreases, the amount of fluid flow does not suddenly increase during the time it takes the operator to recognize the decrease in fluid flow resistance.

Of course, co-operating and intergaging means for releasably securing the collar 11 to the cylinder 1 other than those illustrated, e.g. quarter-turn threads on the cylinder 1 and the collar 11 or a bayonet type coupling, can be employed in place of the projection and slot means described and illustrated. Preferably, however, such means is of the quick connect and disconnect type. Also, means other than the sleeve 6 for attaching a further device to the syringe may be used, and while not preferred, due to the increase in rotation effort required, the piston 3 can be secured to the rod 8 so that it rotates therewith.

Although preferred embodiments of the present invention have been described and illustrated, it will be apparent to those skilled in the art that various modifications may be made without departing from the principles of the invention.

What is claimed is:
1. In a manually actuable syringe comprising:
  a hollow body with an interior wall, a fluid transport opening at one end thereof and a piston receiving opening at the opposite end thereof;
  a piston within said body which has fluid tight engagement with said interior wall, said piston being slidable toward and away from said transport opening;
  a threaded rod secured to said piston and extending at one end from said piston receiving opening; and
  a collar mounted on said rod, said collar having a threaded portion mating with the threads on said rod and said collar and said rod being rotatable relative to each other to cause relative movement of said collar and said rod in a direction longitudinally of said rod;
  the improvement which comprises co-operating and interengaging means on said body and said collar for releasably securing said collar to said body and thereby preventing movement of said collar in a direction extending from one end to the other of said body, whereby rotation of said rod causes said piston to move in said direction including a pair of spaced projections on said body adjacent said opposite end thereof which extend radially outwardly from said body and which are spaced from each other circumferentially of the body, said projections having a circumferential length less than one-half of the circumference of said body, and slots in said collar for receiving said projections, said projections engaging walls of said slots when said collar is adjacent said opposite end and is rotated through a partial turn.
2. A syringe as set forth in claim 1 wherein said projections are disposed on diametrically opposite sides of said body and each projection has a circumferential length not greater than about one-quarter of the circumference of said body.

* * * * *